(12) United States Patent
Thomas et al.

(10) Patent No.: US 8,475,462 B2
(45) Date of Patent: Jul. 2, 2013

(54) ADJUSTABLE EXCISION DEVICE FOR BONES

(76) Inventors: Gareth Thomas, Christchurch (GB); Paul Knox, Dorchester (GB); Daniel Bailey, Chorleywood (GB)

( * ) Notice: Subject to any disclaimer, the term of this patent is extended or adjusted under 35 U.S.C. 154(b) by 618 days.

(21) Appl. No.: 12/591,572

(22) Filed: Nov. 24, 2009

(65) Prior Publication Data

US 2010/0130982 A1    May 27, 2010

(30) Foreign Application Priority Data

Nov. 27, 2008  (GB) .................................. 0821667.3

(51) Int. Cl.
*A61B 17/60* (2006.01)
*A61F 2/00* (2006.01)

(52) U.S. Cl.
USPC .......................................................... 606/87

(58) Field of Classification Search
USPC .................. 606/86 R, 87; 144/286.1, 286.5, 144/306, 307, 308; 248/214, 221.21, 224.51, 248/224.7, 228.1, 231.41, 298.1; 407/29.15, 407/76, 77, 92; 269/37, 313, 314
See application file for complete search history.

(56) References Cited

U.S. PATENT DOCUMENTS

| 4,349,018 | A | * | 9/1982 | Chambers | 606/88 |
| 5,254,119 | A | * | 10/1993 | Schreiber | 606/87 |
| 5,593,411 | A | * | 1/1997 | Stalcup et al. | 606/88 |
| 7,887,542 | B2 | * | 2/2011 | Metzger et al. | 606/87 |

FOREIGN PATENT DOCUMENTS

WO  PCT/US2007/067829    4/2007

OTHER PUBLICATIONS

United Kingdom Intellectual Patent Office Combined Search and Examination Report dated Apr. 7, 2009 in GB0821667.3.

* cited by examiner

*Primary Examiner* — Anu Ramana
(74) *Attorney, Agent, or Firm* — William H. Bollman

(57) ABSTRACT

The present invention provides a device for segmenting a bone. The bone is segmented in two cuts i.e. an initial cut and a final cut. While segmenting the bone, the device is clamped to the bone directly or with the help of a block attached to the bone. An initial cut is taken after the clamping is performed. An upper part of the device is then moved to a predetermined length and the final cut is taken. Thus, the device enables an accurate length of cut to be taken while segmenting the bone. The device also enables varied length of cuts to be taken while segmenting the bone.

20 Claims, 5 Drawing Sheets

ADJUSTABLE EXCISION DEVICE FOR BONES

FIELD OF THE INVENTION

The present invention relates to an adjustable excision device for bones.

BACKGROUND OF THE INVENTION

Osteotomy is a surgical procedure generally used for relieving pain in arthritis, to align a bone which bulges abnormally following a fracture or to shorten or lengthen the bone. Osteotomy involves making singular or multiple cuts into the bone followed by removal of a piece of bone present near a damaged joint.

The piece of bone is typically removed by segmenting the bone with the use of a cutter.

A variety of surgical techniques are required for segmenting a piece of bone. The success of the variety of surgical techniques relies on the preciseness with which a cut is made. An imprecise cut can often lead to severe injuries to patients. Even, unnecessary trauma can be caused to tissues surrounding the piece of bone leading to an increased recovery period.

Generally, cutting guides are employed for straight accurate cuts while performing osteotomy. The cutting guides are fixed on bones/plates with the help of connecting means and have an opening for incorporating a cutter e.g. a saw. The cutter is guided along the opening and a cut is made on one side of a bone for segmenting the bone. For bone segment removal the guide can be removed and then re-fixed in order to make a second cut alternatively guides have two or more slits for cuts. However, as the cutting guides are removed and fixed for each cut, accurate parallelism between cuts is difficult to maintain.

Recent development in the cutting guides involves two set position guides for excising bones. However, the length of cut in these types of cutting guides is fixed restricting them to be used for cuts of variable length.

In the light of the foregoing discussion, there is a need for a device for precise excision of the bones over a varied length. Also, the parallelism between the cuts should be maintained.

A problem has therefore been that the variable lengths of cut are predetermined and little flexibility is provided as to where these may be formed because of the fixed alignment of holes.

One object of the present invention is to provide a device for precise segmenting of a bone.

Another object of the present invention is to provide a device for maintaining parallelism while segmenting a bone.

Yet another object of the present invention is to provide a device for enabling variable length of cuts on a bone.

SUMMARY OF THE INVENTION

According to a first aspect of the invention, there is provided a device for segmenting a bone, the device comprising:
a) a support block comprising one or more recesses;
b) a guide block in slideable connection with the support block, the guide block including one or more holes, wherein, in use, a first hole on the guide block is aligned with a first recess on the support block such that the guide block is able to be positioned to a predetermined length to perform a second operation;
c) a wedge connected to the guide block, wherein the wedge defines an opening for receiving a cutter; and
d) a temporary fixing means for removably connecting the guide block against the support block.

Because apertures or holes can be offset, only corresponding apertures or holes, on an opposite side can be used as they are in register one with another.

Thus if an aperture or hole has been formed in a bone it has been so formed for a reason: namely in order to align with a hole formed on, or in, an opposing surface. Therefore pairs of holes or apertures are formed, in a bespoke manner, so as to be in register one with another. An advantage with this is that for example, when performing a risk assessment, there is less chance that an erroneous shortening of a bone will occur. Alternatively holes may be indicated by an oval, angled slot or other shape of aperture.

In an alternative embodiment these may be stepped or offset one from another in order to unambiguously distinguish two apertures in register one with another.

Ideally variable lengths of cut are predetermined and are formed in this manner because of the alignment of the holes.

A preferred embodiment of the invention will now be described, by way of example only, and with reference to the drawings, in which:

DETAILED DESCRIPTION OF PREFERRED EMBODIMENTS OF THE INVENTION

Figure 1:
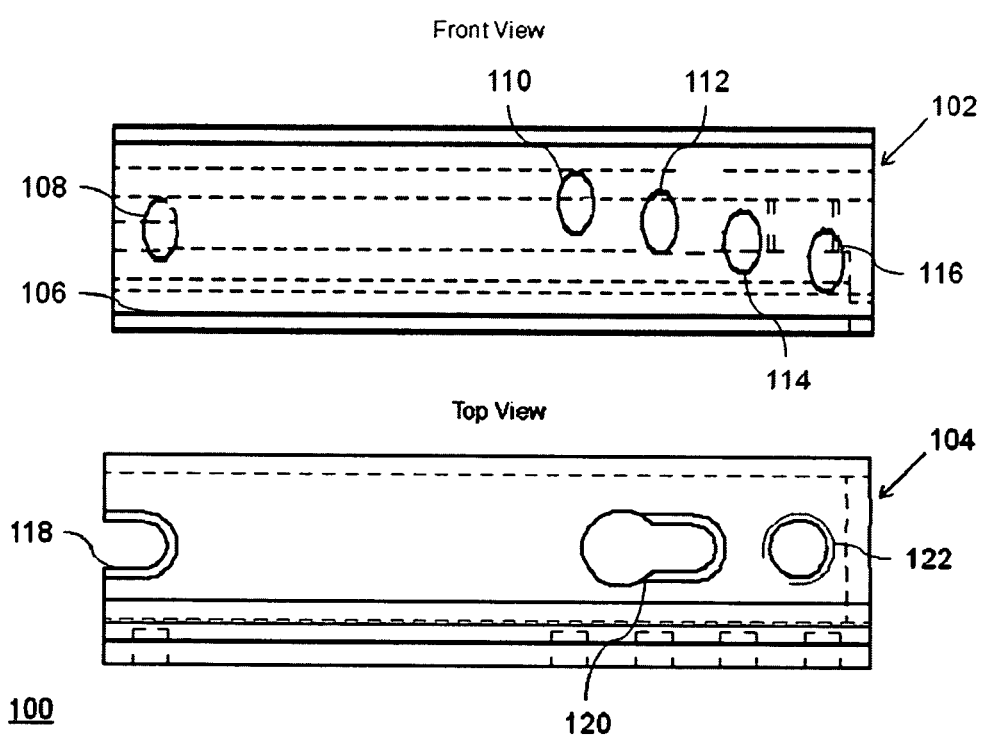
FIG. 1 is an above view of a support block as viewed from in accordance with an embodiment of the present invention.

Referring to the Figures, FIG. 1 is an orthographic projection of a support block 100 viewed from front and top in accordance with an embodiment of the present invention. The support block 100 is generally a block having at least a front surface 102 and a top surface 104. The front surface 102 of the support block 100 includes a dovetail joint 106. The dovetail joint 106 is integrally formed on the front surface 102 of the support block 100.

In an alternate embodiment, the dovetail joint 106 may also be formed as a separate unit and is adapted to be connected to front surface 102. Further, the dovetail joint 106 includes at least one recess 108. Further recesses are shown as 110, 112, 114 and 116. Said recesses 108, 110, 112, 114 and 116 generally have a circular shape. However, the shape of the one or more recesses 108, 110, 112, 114 and 116 can also be square, rectangular, slot or oval or any other suitable shape.

Further, the one or more recesses 108, 110, 112, 114 and 116 include a first recess 108. The first recess 108 acts as a reference for locating the distance of the remaining recesses 110, 112, 114 and 116. The remaining recesses 110, 112, 114 and 116 are spaced at predetermined distances from the first recess 108. For example, the recess 110 is at a horizontal distance of 35.10 mm from the first recess 108. Further, the remaining of the one or more recesses 110, 112, 114 and 116 are spaced apart from one another, typically between 5 and 10 mm and ideally 7 mm horizontally. The predetermined distances are determined based on the length of cut on a bone being segmented.

A line containing centre points of the remaining of the one or more recesses 110, 112, 114 and 116 establishes an angular relationship with a horizontal plane of the front surface 102 of the support block 100. In practice this results in the recesses 108, 110, 112, 114 and 116 all being at slightly different heights from a notional baseline. Points may all be defined in the same plane, with shapes oriented on a different axis, e.g. a triangle could be rotated, for example through 180°, to prevent misalignment with the original form.

Alternatively points could all be located in the same plane, but oriented on a different axis, e.g. a triangle could be rotated through 180° to prevent misalignment with the original form.

Adjacent to front surface 102, is top surface 104 of the support block 100. The top surface 104 includes a plurality of grooves 118, 120 and 122. Grooves may be provided so as to improve purchase. Alternatively holes or recesses may be countersunk in order to provide some sort of improved purchase.

The plurality of grooves 118, 120 and 122 are present on the top surface 104 for enabling the clamping of the support block 100 to the bone or bone plate. Spacing between the plurality of grooves 118, 120 and 122 is based on the desired rigidness of the clamping and the geometry of the bone plate and screws.

Figure 2:
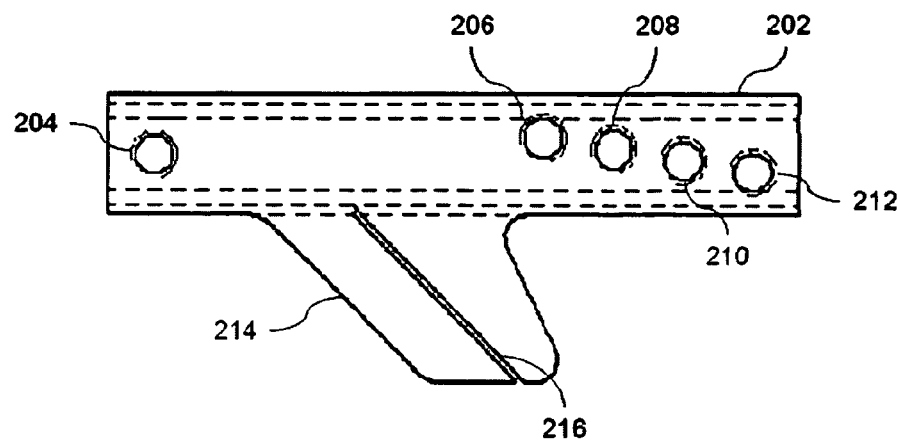
FIG. 2 is a front view of the guide block of FIG. 1.

FIG. 2 is an orthographic projection of a guide block 200 as viewed from a front perspective. Similar to the support block 100, the guide block 200 is a block having at least a front surface 202. The front surface 202 includes one or more holes 204, 206, 208, 210 and 212. It is understood that the or hole or aperture 204, 206, 208, 210 and 212 may be threaded.

A first hole 204 acts as a reference for locating the distance of the remaining one or more holes 206, 208, 210 and 212. The remaining holes 206, 208, 210 and 212 are located at predetermined distances from the first hole 204. The predetermined distances are determined based on the length of cut of the bone being segmented. Further, the predetermined distances between a first hole 204 and the remaining holes 206, 208, 210 and 212 are different than the predetermined distances between the first recess 108 and the remaining of the one or more recesses 110, 112, 114 and 116.

The predetermined distances between the first hole 204 and the remaining holes 206, 208, 210 and 212 are smaller than the predetermined distances between the first recess 108 and the remaining recesses 110, 112, 114 and 116. For example, hole or aperture 206 is at a horizontal distance of 33.10 mm from the first hole or aperture 204.

Further, the remaining of the one or more holes 206, 208, 210 and 212 are spaced apart 6 mm horizontally. A line containing the centre points of the remaining holes 206, 208, 210 and 212 establishes an angular relationship with a horizontal plane of the front surface 202 of the guide block 200. The angular relationship established between the remaining of the one or more holes 206, 208, 210 and 212 and the horizontal plane of the front surface 202 corresponds to the angular relationship established between the remaining of the one or more recesses 110, 112, 114 and 116 and horizontal plane of the front surface 102.

As with the previous block, if the recesses are of a different shape, they can all be kept on the same plane and the recess rotated around a point. The angular relationship is established with a view to enable alignment of the one or more holes 204, 206, 208, 210 and 212 only with its corresponding one or more recesses 108, 110, 112, 114 and 116. For example, the hole 206 can be only aligned with its corresponding recess 110. This enables precise alignment by avoiding any erroneous alignment of recesses 110, 112, 114 and 116 and the apertures or holes 206, 208, 210 and 212.

To further enhance the guide block 200, the remaining holes 206, 208, 210 and 212 are dimensioned based on the first hole 204. The dimensioning enables a user to select a hole from the group of holes 206, 208, 210 and 212 based on the length of cut on the bone being segmented.

Guide block 200 further includes a wedge 214. The wedge 214 is integrally formed with the guide block 200. The wedge 214 is formed in the guide block 200 for incorporating cutter 216. The cutter is incorporated in an opening 216 present in the wedge 214. An example of the cutter is a saw.

A dovetail joint could be used so that the wedge may slide down and be located closer to the bone. In an alternate embodiment, the wedge 214 can be a separate unit. The separate unit can then be connected to the guide block 200. Examples of the connection of the separate unit and the guide block 200 include, but are not limited to, a riveted joint, a screwed joint, a welded joint, a glued joint, a brazed joint, a soldered joint, and a magnetic joint.

The guide block 200 also includes a slot for incorporating the dovetail joint 106. The slot is present on a back surface of the guide block 200.

Figure 3:
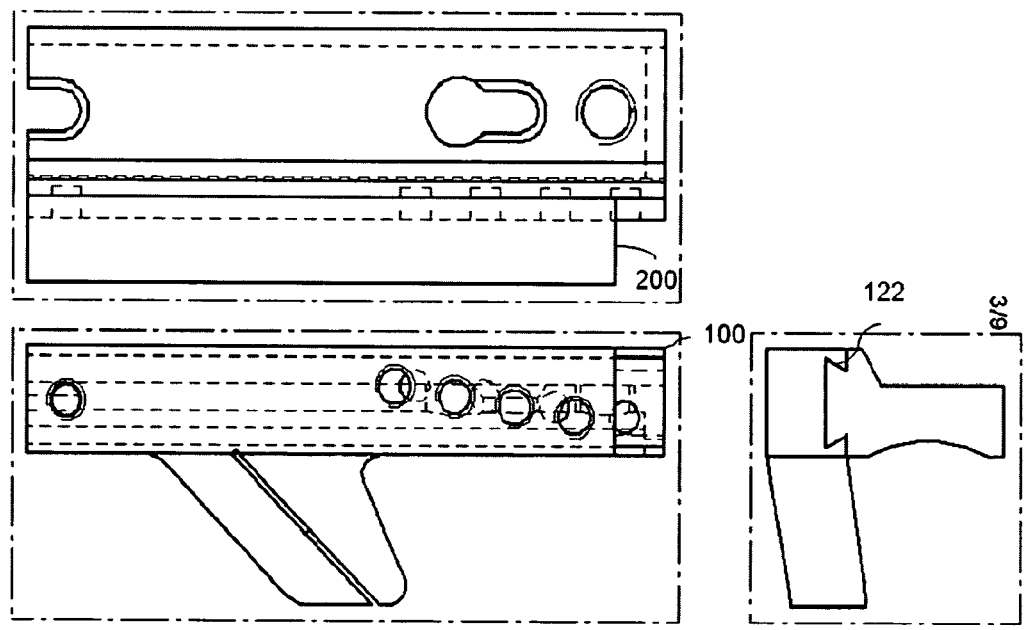
FIG. 3 is an orthographic projection of an assembly of a support block and a guide block as viewed from front, top and side.

FIG. 3 is an orthographic projection of an assembly 300 of a support block 100 and a guide block 200 as viewed from front, top and side in accordance with an embodiment of the present invention. The assembly 300 of the support block 100 and the guide block 200 is performed by displacing the guide block 200, with respect to the support block 100 in a slideable manner. The slot present on the back surface of the guide block 200 is slid through the dovetail joint 106 present on the front surface 102 of the support block 100. The dovetail joint 106 permits only a lateral movement of the guide block 200 with respect to the support block 100.

Figure 4:
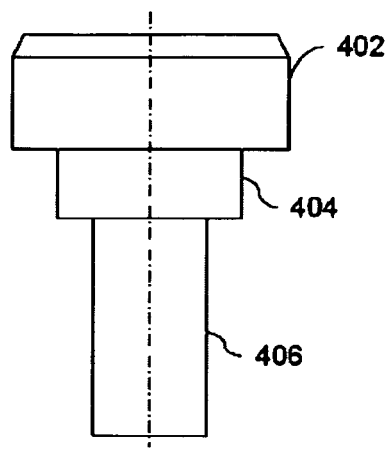
FIG. 4 is an orthographic projection of a stopper.

FIG. 4 is an orthographic projection of a stopper 400 as viewed from front in accordance with an embodiment of the present invention. The stopper 400 includes a top surface 402, an intermediate surface 404 and a bottom surface 406. The top surface 402 of the stopper 400 is ergonomically designed for the comfort of a user. The ergonomic design of the top surface 402 facilitates easy handling of the stopper 400 by the user. The intermediate surface 404 is located below the top surface 402. The intermediate surface 404 may be threaded for retaining the stopper 400 in a fixed position. The bottom surface 406 can also be used for retaining the stopper 400 in a fixed position and it is understood that the entire length may be threaded.

Figure 5:
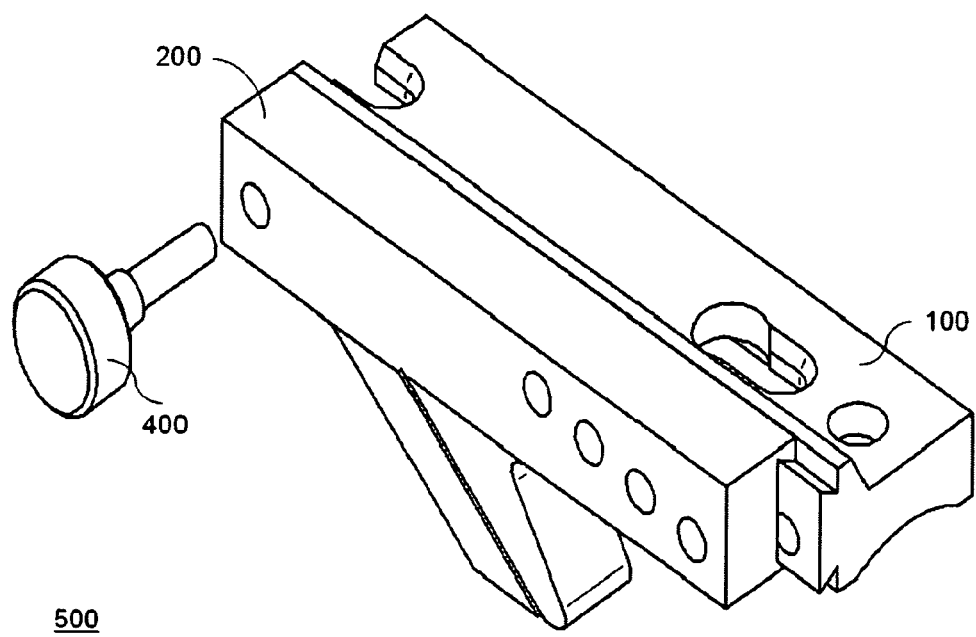
FIG. 5 is an isometric view of an assembly of a guide block and a support block.

FIG. 5 is an isometric view of an assembly 500 of a guide block 200 and a support block 100 in an embodiment of the present invention. The isometric view is shown for better understanding of the assembly of the guide block 200 and the support block 100 as shown in FIG. 3. Further, the isometric view of the stopper 400 is also shown.

Figure 6:
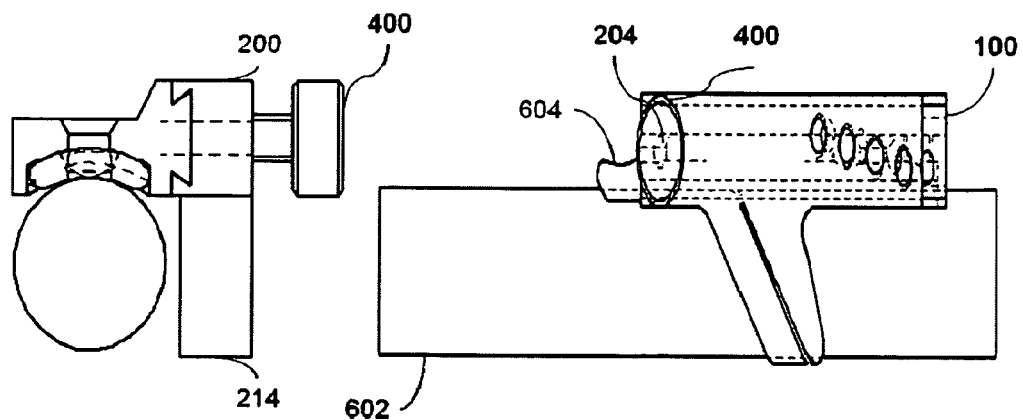
FIG. 6 is an orthographic projection of an assembly, depicting the position of a guide block during a first operation.

FIG. 6 shows an assembly 600 depicting the position of a guide block 200 during a first operation with an embodiment of the present invention. The first operation is performed for providing a first cut on a bone 602 to be segmented. In use a portion of the bone 602 is covered with a plate 604. The plate 604 is provided for retaining the clamping of the support block. It secures the bone; and is remains in situ after the procedure as an implant.

The support block 100 is clamped on the plate 604 with the help of the plurality of grooves 118, 120 and 122 present on the support block 100. In an alternate embodiment, the support block 100 can be directly clamped on the bone 602.

Once the clamping is performed, the guide block 200 is slid through the dovetail joint 106 present on the support block 100. The guide block 200 is slid for aligning the first hole 204 with the first recess 108. When the first hole 204 and the first recess 108 are aligned, the remaining of the one or more holes 206, 208, 210 and 212 are offset to the remaining of the one or more recesses 110, 112, 114 and 116.

After the alignment is performed, the stopper 400 is inserted through the first hole 204 and the first recess 108. Threads present on the intermediate surface 404 are mated with the threads present in the first hole 204. The bottom surface 406 of the stopper 400 is mated in the first recess 108. Insertion of the stopper 400 enables restriction of movement of the guide block 200 with respect to the support block 100. The movement of the guide block 200 is restricted so as to permit the first operation to be performed.

The first operation is performed by taking a first cut on the bone 602 with the help of the cutter. The cutter is inserted in the opening 216 of the wedge 214 for taking the first cut on the bone 602.

Figure 7:
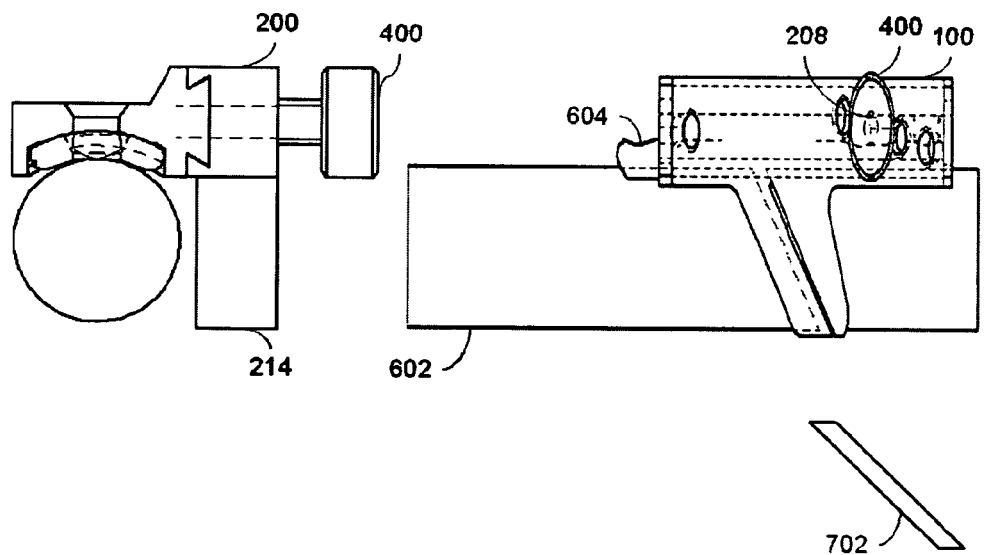
FIG. 7 is an orthographic projection of an assembly depicting the position of a guide block during a second operation.

FIG. 7 is an orthographic projection of an assembly 700 depicting the position of a guide block 200 during a second operation of the present invention. The second operation is performed for providing a second cut on the bone 602. The second cut on the bone 602 is made after determining the length of cut on the bone 602 being segmented. In accordance with an exemplary embodiment of the present invention, if the length of the cut to be taken is determined to be 3.5 mm; a second hole, for example, aperture or hole 208 is selected.

Different holes can be selected from one or more holes 206, 208, 210 and 212 based on the requisite length of the cut on the bone 602. After the selection, the stopper 400 is removed from the first recess 108 and the first hole 204. The removal of the stopper 400 thus enables the movement of the guide block 200 with respect to the support block 100 for aligning the second hole 208 with a second recess 112. The alignment of the second hole or aperture 208 and the second recess 112 is achieved by moving the guide block 200. Similar to the first operation, when the second hole 208 is aligned with the second recess 112 the remaining holes 204, 206, 210 and 212 are offset with respect to the one or more recesses 108, 110, 114 and 116. The offset thus permits a user to insert the stopper 400 only in the second hole 208 and the second recess 112.

Continuing with this example, after alignment, the stopper 400 is inserted through the second hole 208 and the second recess 112. The insertion of the stopper 400 is similar to the insertion done in the first operation. As the stopper 400 is inserted, the second cut is made in the bone 602. The second cut is made on the bone 602 by the cutter. A segmented piece of bone 702 is then removed for performing further observations/procedures. This alignment procedure may be similar for aligning for example recess 110 with hole 206; or recess 114 with hole 210; or recess 116 with hole 212.

Figure 8:
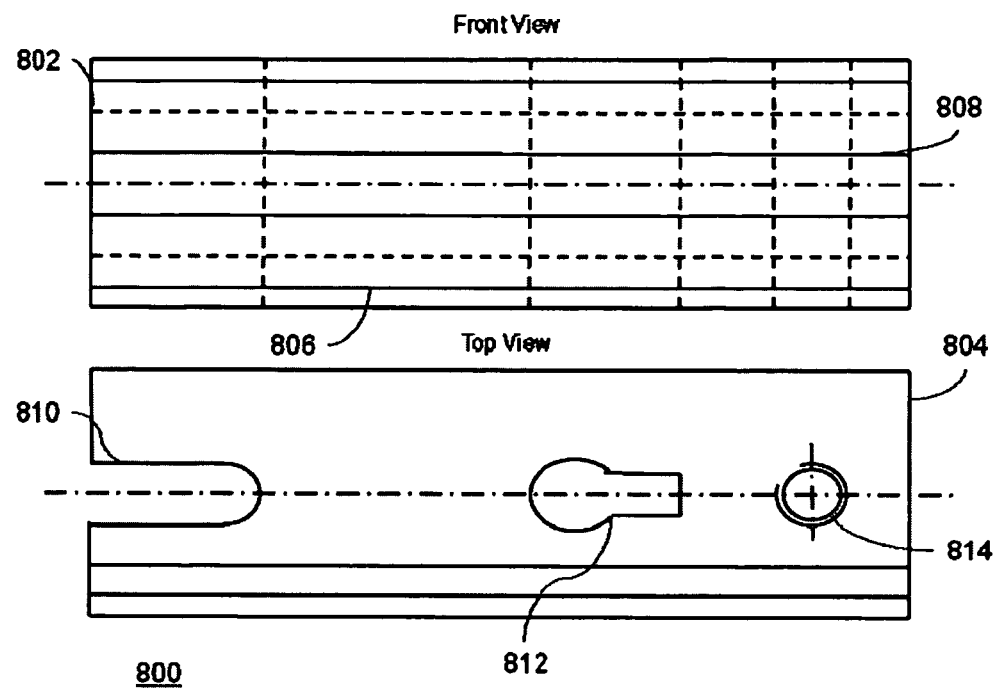
FIG. 8 is an orthographic projection of a support block viewed from front and top in an alternate embodiment of the present invention.

FIG. 8 is an orthographic projection of a support block 800 viewed from front and top in an alternate embodiment of the present invention. The alternate embodiment obviates the need of the one or more recesses on the support block 800. As shown in FIG. 8, the support block 800 includes a front surface 802, and a top surface 804. The front surface 802 further includes a dovetail joint 806. The dovetail joint 806 is integrally formed in the front surface 802 of the support block 800. In an embodiment, the dovetail joint 806 can also be a separate unit and can be connected to the front surface 102. Further, the dovetail 806 includes a recess 808. The recess 808 is extended over an entire length of the support block 800.

Adjacent to the front surface 802 of the support block 800 is the top surface 804. The top surface 804 on the support block 800 includes a plurality of grooves 810, 812 and 814. The plurality of grooves 810, 812 and 814 on the support block 800 serve similar function as that performed by the plurality of grooves 118, 120 and 122 on the support block 100.

The plurality of grooves 810, 812 and 814 are used for securing the support block 800 on the bone 602. The plurality of grooves 810, 812 and 814 can be used to secure the support block 800 directly to the bone 602 or via a bone plate 604. In one embodiment, the plurality of grooves 810, 812 and 814 can be used to secure the support block 800 to the block 604 placed on the bone 602.

Figure 9:
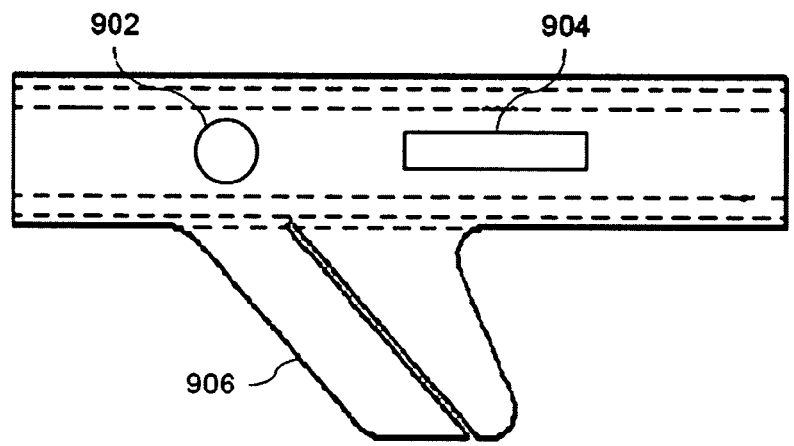
FIG. 9 is an orthographic projection of a guide block of FIG. 8 viewed from front.

FIG. 9 is an orthographic projection of a guide block 900 viewed from front in accordance with an alternative embodiment of the present invention. The alternative embodiment obviates the need of the one or more holes on the guide block 900. The guide block 900 is in slideable connection with the support block 800. The guide block 900 includes a first hole 902, a scale 904 and a wedge 906. The first hole 902 may be threaded internally for incorporating the intermediate surface 404 of the stopper 400. The stopper 400 restricts the movement of the guide block 900 by passing through the hole 902 and then through the recess 808 present on the support block 800. The movement of the guide block 900 is restricted, based on the distance measured by the scale 904. Examples of the scale include but are not limited to an analogue scale and a digital scale. The scale 904 is used for measuring the distance travelled by the guide block 900 during the first operation and the second operation. The first operation and the second operation are performed by cutting the bone 602 with the cutter. The cutter is incorporated in an opening present in the wedge 906.

During the first operation, the support block 800 is clamped to the bone 602 or on the block 604 provided on the bone 602. The clamping is performed with the use of fasteners. After the clamping, a slot or groove present on a back surface of the guide block 900 slidably receives dovetail joint 806 present on the support block 800. The dovetail joint 806 enables a lateral movement of the guide block 900 with respect to the support block 800. The lateral movement of the guide block 900 can be measured with the help of the scale 904. The scale 904 is used to locate the guide block 900 for a first cut. Further, the stopper 400 is inserted through the aperture or hole 902 and the recess 808, thus restricting the movement of the guide block 900. The first cut is then made by inserting the cutter through the opening present in the wedge 906.

Following the first cut, the stopper 400 is removed from the recess 808 and the hole 902 for enabling the movement of the guide block 900. The guide block 900 is then moved through a predetermined length for the second operation. The predetermined length is measured by the scale 904. The predetermined length corresponds to the length of cut of the bone 602 being segmented. The stopper 400 is again inserted through the hole 902 and the recess 808 for performing the second operation. In the second operation, the cutter is inserted through the opening present in the wedge 906 and the second cut is taken. The second cut results in the segmentation of the bone 602 and a piece of bone is removed thereof.

While the preferred embodiments of the invention have been illustrated and described, it will be clear that the invention is not limited to these embodiments only. Numerous modifications, changes, variations, substitutions and equivalents will be apparent to those skilled in the art without departing from the spirit and scope of the invention as described in the claims. Other metals that could be used include anything that is inert or brass or $Ti_6Al_4V$.

Further, it should be clearly understood that the form of the present invention described herein and shown in the figures of the accompanying drawing are illustrative only and are not intended to limit the scope of the present invention. Thus the scope of the invention should be determined by the appended claims and their legal equivalents, rather than by the examples given.

For example it may be desirable to have a dovetail joint for sliding down to the bone.

The invention claimed is:

1. A device for cutting a predetermined thickness of a piece of bone, comprising:
   a support block which in use is fixed relative to the bone, the support block has a plurality of recesses adapted to receive a stopper; and
   a guide block having a wedge defining an opening for receiving a cutter to guide cuts, the guide block and support block being arranged to permit relative movement there-between, the guide block includes a plurality of holes, only one of which holes is alignable with an associated recess on the support block, so that a stopper is able to pass through the hole into the recess at a unique configuration of the guide block and support block where the hole aligns with the associated recess, thereby arresting relative movement between the blocks, such that in use at a first predetermined configuration of the blocks, the cutter makes a first cut, and at a second configuration of the blocks the cutter makes a second cut, the two cuts being parallel one to another so as to define the predetermined thickness of the piece of bone.

2. The device as recited in claim 1, wherein the stopper may comprise a threaded portion.

3. The device as recited in claim 1, wherein the stopper, the guide block, the support block and the wedge are made of a metal selected from a group consisting of steel, stainless steel, titanium, brass, Ti6Al4V and aluminum.

4. The device as recited in claim 1, wherein the plurality of holes consist of a first hole and remaining holes and the plurality of recesses consist of a first recess and remaining recesses, where the remaining holes are at predetermined distances from the first hole, and remaining recesses are at larger predetermined distances from the first recess than the corresponding predetermined distances separating the first hole and the remaining holes.

5. The device as recited in claim 1, further comprising a dovetail joint enabling the sliding of the guide block with respect to the support block.

6. The device as recited in claim 1, wherein the support block further comprises a plurality of recesses, holes or grooves on a top surface of the support block the plurality of grooves enabling the clamping of the support block to a block placed on the bone.

7. The device as recited in claim 1, wherein the wedge is integrally connected with the guide block.

8. The device as recited in claim 1, wherein a connection connecting the wedge and the guide block is selected from a group consisting of a riveted joint, a screwed joint, a welded joint, a glued joint, a brazed joint, a soldered joint and a magnetic joint.

9. The device as recited in claim 1, wherein the cutter is a saw.

10. The device as recited in claim 1, wherein one hole of the plurality holes on the guide block can only be aligned with one recess of the plurality of recesses on the guide block while performing at least one of the first cut and the second cut.

11. The device as recited in claim 1, further comprising a scale to determine the position of the guide block along a longitudinal axis of the support block.

12. The device as recited in claim 11, wherein the scale can be selected from a group consisting of an analogue scale and a digital scale.

13. A method for segmenting a bone, the bone being segmented in two cuts i.e. a first cut and a second cut, the method comprising the steps of:
   a. connecting a support block to the bone, wherein the support block comprises a plurality of recesses;
   b. sliding a guide block received in a dovetail joint of the support block, wherein the guide block comprises a plurality of holes;
   c. aligning a first hole of the plurality of holes on the guide block with a first recess of the plurality of recesses on the support block for performing the first cut; and
   d. moving the guide block for performing the second cut.

14. The method as recited in claim 13, further comprising inserting a stopper through the first hole and the first recess after alignment.

15. The method as recited in claim 13, wherein the step of moving the guide block further comprises selecting a second hole of the plurality of holes on the guide block and moving the guide block till the second hole of the plurality of holes on the guide block is aligned with a second recess of the plurality of recesses on the support block.

16. The method as recited in claim 15, wherein the selection of the second hole is based on the length of the cut on the bone being segmented.

17. The method as recited in claim 15, further comprising inserting a stopper in the second hole of the remaining of the one or more holes on the guide block.

18. The method as recited in claim 13, wherein the guide block is moved to the predetermined length using a scale to determine the position of the guide block along a longitudinal axis of the support block.

19. The method as recited in claim 13, wherein the predetermined length corresponds to the length of the cut on the bone being segmented.

20. The method as recited in claim 13, further comprising removing the bone segment after performing the second cut.

* * * * *